(12) United States Patent
Genc

(10) Patent No.: US 9,706,945 B2
(45) Date of Patent: Jul. 18, 2017

(54) RESPIRATION RATE DETERMINATION IN IMPEDANCE PNEUMOGRAPHY

(71) Applicant: GENERAL ELECTRIC COMPANY, Schenectady, NY (US)

(72) Inventor: Sahika Genc, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 580 days.

(21) Appl. No.: 14/225,222

(22) Filed: Mar. 25, 2014

(65) Prior Publication Data
US 2015/0272474 A1    Oct. 1, 2015

(51) Int. Cl.
- A61B 5/08       (2006.01)
- A61B 5/0402     (2006.01)
- A61B 5/00       (2006.01)

(52) U.S. Cl.
CPC .......... *A61B 5/0809* (2013.01); *A61B 5/7203* (2013.01); *A61B 5/725* (2013.01); *A61B 5/7221* (2013.01); *A61B 5/0402* (2013.01); *A61B 5/0816* (2013.01); *A61B 5/7271* (2013.01)

(58) Field of Classification Search
CPC ......... A61B 5/08; A61B 5/0809; A61B 5/725; A61B 5/7203; A61B 5/7221; A61B 5/0402; A61B 5/0816; A61B 5/7271
See application file for complete search history.

(56) References Cited

U.S. PATENT DOCUMENTS

| | | | |
|---|---|---|---|
| 2005/0251056 A1 | 11/2005 | Gribkov et al. | |
| 2006/0161069 A1* | 7/2006 | Li | A61B 5/04525 600/515 |
| 2008/0275337 A1 | 11/2008 | Fossan et al. | |
| 2010/0016682 A1 | 1/2010 | Schluess et al. | |
| 2010/0022903 A1 | 1/2010 | Sitzman et al. | |
| 2010/0268093 A1 | 10/2010 | Balji et al. | |
| 2011/0172504 A1* | 7/2011 | Wegerich | A61B 5/0205 600/301 |
| 2011/0245711 A1* | 10/2011 | Katra | A61B 5/0537 600/547 |
| 2011/0257551 A1 | 10/2011 | Banet et al. | |
| 2012/0123232 A1 | 5/2012 | Najarian et al. | |
| 2012/0165622 A1 | 6/2012 | Rodr Guez Ib Nez et al. | |
| 2014/0364756 A1* | 12/2014 | Brockway | A61B 7/00 600/513 |

OTHER PUBLICATIONS

Nemati et al., "Data Fusion for Improved Respiration Rate Estimation", EURASIP Journal on Advances in Signal Processing, pp. 1-10, vol. 2010, Issue 10, Jun. 8, 2010.

Sankar et al., "Performance Study of Various Adaptive Filter Algorithms for Noise Cancellation in Respiratory Signals", Signal Processing, An International Journal (SPIJ), pp. 267-278 vol. 4, Issue 5, Dec. 20, 2010.

* cited by examiner

*Primary Examiner* — Navin Natnithithadha
*Assistant Examiner* — Eric Messersmith
(74) *Attorney, Agent, or Firm* — Pabrita K. Chakrabarti

(57) ABSTRACT

A system for monitoring respiration, and a method for determining respiration rate, is disclosed. In one embodiment, the respiration rate is determined from a power spectral density template that is updated, or not, based on whether a power spectral density for a current window of in-band filtered impedance respiration signal is determined to be noisy or not.

18 Claims, 6 Drawing Sheets

RESPIRATION RATE DETERMINATION IN IMPEDANCE PNEUMOGRAPHY

BACKGROUND

The subject matter disclosed herein relates to determining a signal quality related to a monitored physiological measurement.

Respiration may be one of many physiological functions that are monitored in order to obtain an overall assessment of a patient's physiological status. Impedance pneumography is one technique that is used to measure respiration and may typically be performed in conjunction with the measurement of electrocardiograph (ECG) signals. The accuracy of impedance pneumography measurements, however, may be impacted by various factors, such as patient or other motion, airway obstruction, changes in posture of the patient, and heartbeat artifacts.

Due to the sensitivity of impedance pneumography to heartbeat and motion artifacts, patient respiration may be detected inaccurately, which in turn can lead to technically false alarms, i.e., false alarms due to poor signal quality. It may, therefore, be desirable to reduce the incidence of such false alarms and to improve the overall accuracy of the respiration monitoring functionality.

BRIEF DESCRIPTION

In one embodiment, a method is provided for deriving a respiration rate. In accordance with this method, an impedance respiration signal is acquired. A series of sets of windowed data from the impedance respiration signal are generated. Each window of data comprises data points acquired over a specified duration and is offset from a preceding window by a fixed interval. The impedance respiration signal is filtered through at least an in-band filter to generate an in-band filtered signal. For each window of in-band filtered signals, a respective power spectral density is generated. Whether the respective power spectral density for a current window is noisy or not noisy is determined. If the respective power spectral density for the current window is not noisy, a previous power spectral density template is updated based on the respective power spectral density for the current window to generate a current power spectral density template. If the respective power spectral density for the current window is noisy, the previous power spectral density template is not updated. At least one peak is identified along with the corresponding frequencies and powers associated with the identified peaks within the current power spectral density template. A respiration rate is determined based on the at least one identified peak.

In a further embodiment, a non-transitory, computer-readable medium is provided that is configured to store one or more routines executable by a processing system. The routines, when executed, cause acts to be performed comprising: applying an in-band filter to an impedance respiration signal to generate an in-band filtered signal; generating a respective power spectral density for each of a series of windows of the in-band filtered signal, wherein each window comprises data points acquired over a specified duration and is offset from adjacent windows by a fixed interval; processing the respective power spectral density for each window in sequence to determine whether the respective power spectral density for each window is noisy or not noisy; updating, if the respective power spectral density for a current window is not noisy, a previous power spectral density template based on the respective power spectral density for the current window to generate a current power spectral density template; and determining a respiration rate based on one or more peaks identified in the current power spectral density template.

In an additional embodiment, a physiological monitoring system is provided. The physiological monitoring system comprises a memory storing one or more routines and a processing component configured to execute the one or more routines stored in the memory. The one or more routines, when executed by the processing component, cause acts to be performed comprising: acquiring an impedance respiration signal; generating a series of data windows from the impedance respiration signal, wherein each data window comprises data points acquired over a specified duration and is offset from a preceding window by a fixed interval; filtering the impedance respiration signal through at least an in-band filter to generate an in-band filtered signals; generating a respective power spectral density for each window of in-band filtered signals; determining whether the respective power spectral density for a current window is noisy or not noisy; updating, if the respective power spectral density for the current window is not noisy, a previous power spectral density template based on the respective power spectral density for the current window to generate a current power spectral density template; and determining a respiration rate based the current power spectral density template.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
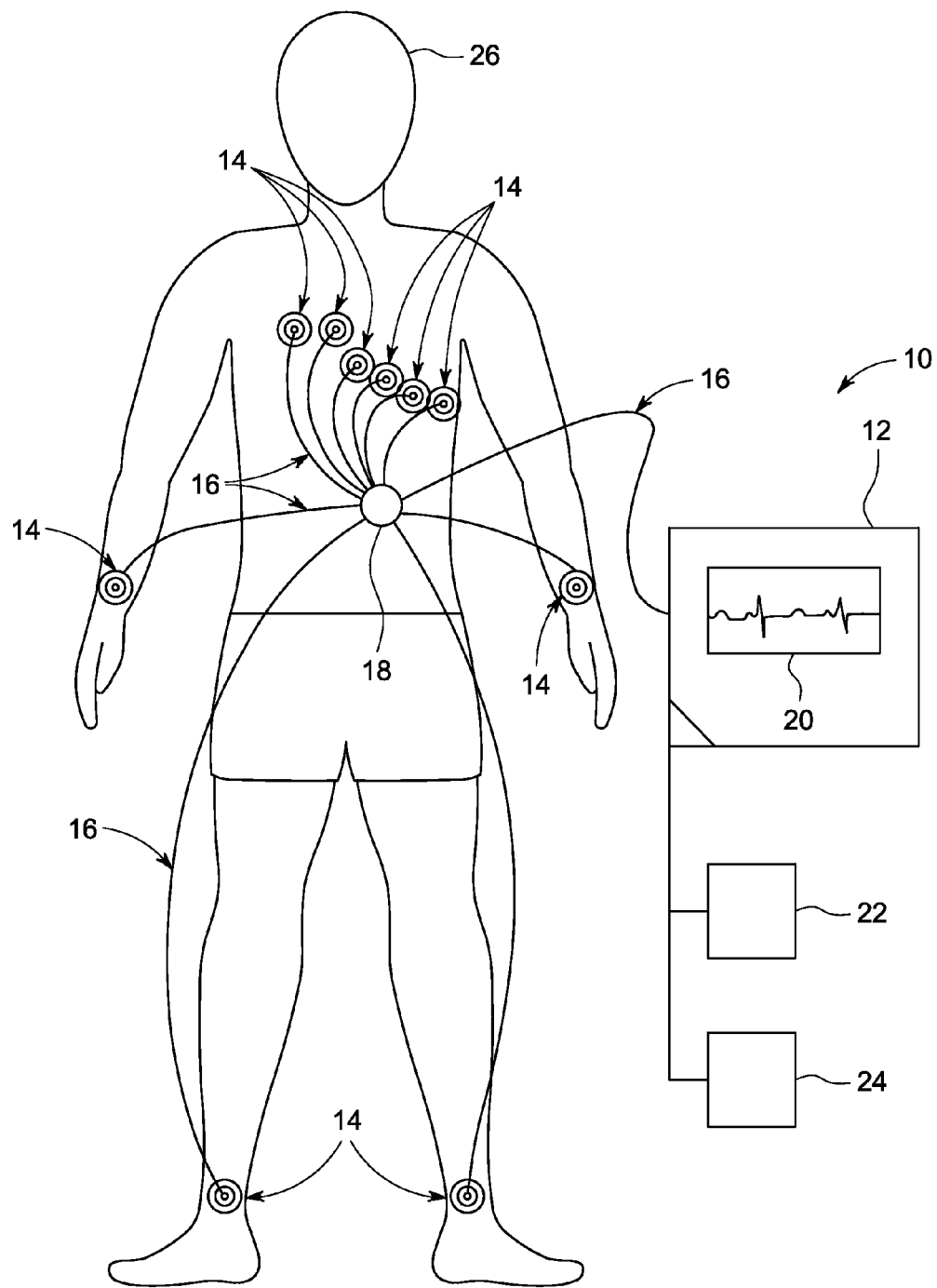
FIG. 1 illustrates an embodiment of an electrocardiograph having impedance pneumography functionality, including sensors coupled to a patient.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Impedance pneumography is an approach typically utilized to monitor respiration. In particular, impedance pneumography typically senses transthoracic electrical impedance variations from the ribcage to provide an indirect measure of ventilation. The electrical resistance of the lungs increases during inspiration (and conversely decreases during expiration) as a result of changes in the gas volume of the chest in relation to the fluid volume and changes in the length of the conductive paths during respiration.

In practice, impedance pneumography may be implemented in conjunction with electrocardiography (ECG), and thus may be a function performed on an ECG system. In particular, to measure respiration rate, a small-amplitude, high-frequency current is injected into the body of the patient through a pair of electrodes (i.e., leads) which can be used to simultaneously record the electrocardiogram. The resulting voltage across the electrodes then is demodulated to obtain impedance measurements. The frequency of the impedance measurements is linearly correlated with the respiration rate. As discussed above, due to the sensitivity of impedance pneumography to heartbeat and motion artifacts, respiration beats may be detected inaccurately, which in turn can lead to technically false alarms, i.e., false alarms due to poor signal quality.

With the foregoing in mind, the present approach relates to the measurement of signal quality and to using the measured signal quality to improve the measurement of respiration rate using impedance pneumography. In particular, a signal quality indicator for impedance pneumography, as discussed herein, may be generated based upon the principle of reconstructing a signal that is less noisy or free of noise and subtracting the reconstructed signal from the raw waveform signal, assuming that the noise is additive, and mapping the remaining signal to an interval of 0-1.

If the result of this mapping is above a specified threshold, then the signal quality is deemed to be acceptable (i.e., the signal quality is deemed to be good). If the result of the mapping is below the specified threshold, then the signal quality is deemed to be unacceptable (i.e., the signal quality is deemed to be bad). Tests on various data sets have shown that a threshold signal quality indicator (SQI) value can be utilized to arbitrate arrhythmia or parameter alarms to reduce false positive alarms while keeping all true alarms generated by the legacy alarm algorithms. That is, the use of the signal quality indicator can improve the specificity of the legacy arrhythmia and parameter alarm algorithms without degrading their sensitivity.

With the foregoing general discussion in mind, and turning to the figures, FIG. 1 illustrates a system 10 (e.g., an electrocardiograph system or dedicated impedance pneumography system) capable of performing impedance pneumography, in accordance with present embodiments. Specifically, the system 10 includes a monitor 12, sensors (i.e., electrodes or leads 14), communication cables 16, a cable junction 18, a display 20, a processor 22, and a memory 24. In the illustrated embodiment, the leads 14 are coupled to different areas on a patient 26 (e.g., the torso, right arm, left arm, right leg, and left leg). Different numbers of leads 14 may be provided in different embodiments (e.g., 3-, 5-, and 12-lead systems). Coupling between the patient 26 and the leads 14 may be achieved by an adhesive portion (e.g., a tacky base layer) of the leads 14 or the like.

The leads 14 are coupled to the cable junction 18 via the individual communication cables 16 and the cable junction 18 couples with the monitor 12 via a single one of the communication cables 16. In other embodiments, different communication arrangements may be provided. For example, each lead 14 may directly communicate with the monitor 12. In some embodiments, each lead 14 may communicatively couple with the monitor 12 wirelessly or couple with the cable junction 18, which may wirelessly communicate with the monitor 12. Additionally, in some embodiments a different number or placement of the leads 14 may be utilized.

The system 10 depicted also includes a data processing component 22 (e.g., one or more processors) configured to receive and/or process the electrical signals communicated via the leads 14 and cables 16. For example, the data processing component 22 may execute one or more stored processor-executable routines that may process digitized signals derived from the measured electrical signals, may process the data to generate an impedance pneumography signal quality indicator, may generate a respiration rate taking into account signal quality information, and/or may trigger an audible or visual alarm when appropriate.

The routines executed by the processing component 22 and/or the data processed by the processing component 22 may be stored on a storage component (i.e., memory 22 or other suitable storage structures in communication with the processing component 22). Suitable storage structures include, but are not limited to, one or more memory chips, magnetic or solid state drives, optical disks, and so forth, suitable for short or long-term storage. The storage component may be local or remote from the data processing component 22 and/or system 10. For example, the storage component may be a memory 24 or storage device located on a computer network that is in communication with the data processing component 22. In the present context, the storage component may also store programs and routines executed by the data processing component 22, including routines for implementing the presently disclosed approaches for determine signal quality and/or measuring a respiration rate.

Figure 2:
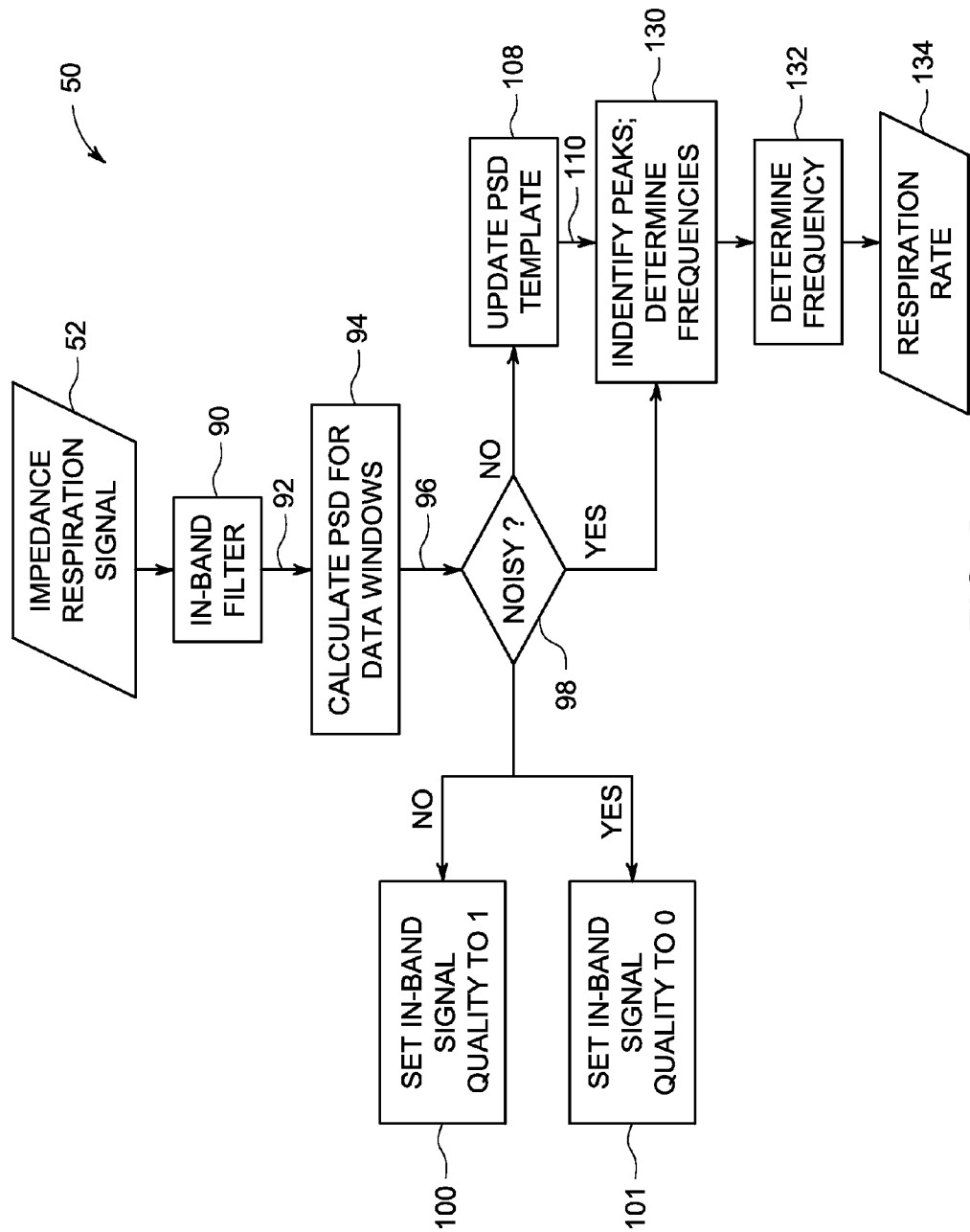
FIG. 2 is a flow chart depicting control logic for the calculation of a respiration rate, in accordance with aspect of the present disclosure.

With the foregoing in mind, FIG. 2 depicts control logic of an algorithm 50 that may be stored and implemented on the system 10 or on a system having access to data generated by the system 10. In general, the algorithm 50, as described in greater detail below, reconstructs a noise-free or reduced noise signal using in-band frequencies. The reconstructed signal is based on sequentially acquired windows of data points that are each evaluated for signal quality and, if deemed to be of acceptable quality (i.e., sufficiently noise free), are used to update a set of existing data (i.e., a template) also deemed to be of acceptable quality to generate the reconstructed signal, which may be used to derive a respiration rate. If a window of data is deemed to be of unacceptable quality (i.e., noisy), no update of the template is performed.

In accordance with one embodiment of algorithm 50, an impedance respiration signal 52 is collected at a specified frequency (such as at 60 Hz or at frequencies that are multiples of 60 Hz) as an input to the algorithm 50. In one embodiment, the algorithm 50 starts producing a signal quality indicator or measure after 24 seconds of data acquisition (i.e., after collection of 1,440 data points). The interval of data acquisition may be varied in other implementations, however, and 24 seconds is merely one example, of a suitable interval. For example, this data acquisition interval is a design parameter that can be optimized. In one implementation, the data acquisition window is optimized to be a duration (i.e., window) in which at least two breaths are observed within the selected window size. After the first window of data is acquired (whether of 24 second duration or otherwise) the signal quality indicator value is generated at the same rate (i.e., 60 Hz) as waveform points.

In the depicted filtering step (block 90) is performed using an in-band pass filter having low- and high-frequency cutoffs. In one example, the low-frequency cutoff is at a frequency of 0.1 Hz such that signal below this frequency is not passed and the high-frequency cutoff is at a frequency of 0.8 Hz such that signal above this frequency is not passed. For example, in one implementation, the in-band pass filtering step would pass signal within a range of 0.1 and 0.8 Hz, but would not pass signal outside this range. In this example, the low and high frequency cutoffs of 0.1 Hz and 0.8 Hz, respectively, correspond to breathing rates between 6 and 48 breaths per minute. The in-band filtered signal 92 may be used both in the determination of signal quality and respiration rate.

In one implementation, the output 92 of the in-band filter is stored in windows of 24-second duration (i.e., each window corresponds to 24*60 data points, or 1,440 data points) where a new window is generated every 2 seconds. In the depicted example, a power spectral density (PSD) 96 of each 24-second window is calculated (block 94), such as using fast Fourier algorithm. If the power spectral density 96 of the most recent window is not determined (block 98) to be noisy then an updated template 110 is generated (block 108) based on the previous PSD template and the current PSD 96. For example, in one embodiment the new PSD template 110 is generated as a weighted sum of the current PSD (i.e., the PSD for the most recent 24-second window of data) and the previous PSD template. In one such implementation, the current PSD may be weighted higher than the previous PSD template when computing the updated PSD template 110 such that the more current data is overweighted relative to older data. For example, in one embodiment the current PSD may be given a weight of 0.6 while the previous PSD template is given a weight of 0.4. If, however, the PSD 96 of the most recent 24-second window is determined to be noisy, then the previous PSD template is not updated (i.e., step 108 is not performed and updated PSD template 110 is not generated).

With respect to the determination (block 98) of whether a PSD 96 is noisy, in one implementation, a set of the most recent good PSD templates (e.g., 3, 4, or 5 of the most recent good PSD templates) are stored in a memory (e.g., memory 24) and are used to determine (block 98) whether each PSD 96 is noisy or not. In one such embodiment, to determine if a PSD 96 is noisy, a correlation vector is generated from the stored PSD templates (e.g., the most recent 5 PSD templates). In one such embodiment, if the mean (or, alternatively, the median, mode, max, or min) of the generated correlation vector is greater than a pre-selected threshold, then the PSD 96 being evaluated is determined (block 98) to not be noisy. If not, then the PSD 96 is considered noisy and is not used to update (block 108) the most recent PSD template. If the PSD template is updated (block 108), then a measure or indicator of the in-band signal quality is considered to be 1 (block 100) for the interval of interest (e.g., 2 seconds). Conversely, if the PSD 96 is determined to be noisy and the PSD template is not updated, the in-band signal quality is considered to be 0 (block 101) for the interval of interest.

In one implementation, different types of signal quality indicators or measures may be combined to generate an overall indicator of respiration signal quality associated with the impedance respiration signal 52. In one embodiment, larger weights may be applied to different signal quality indicators to determine the overall respiration signal quality. Further, one or more of the component signal quality measures or indicators may be moving average filtered to smooth the respective outputs and reduce hysteris prior to combination. Thus, the final respiration signal quality indicator may include the combined effects (weighted or otherwise) of different quality indicators in one measure that may be used in evaluating the overall signal quality of the impedance respiration signal 52 at a given time.

The respiration signal quality may be displayed along with the respiration data, such as on monitor 12. For example, the respiration signal quality may be displayed as a numeric value and/or as a waveform for a caregiver to review in conjunction with any displayed respiration data. In such embodiments, the displayed respiration signal quality may allow a caregiver to evaluate or arbitrate an alarm condition based on the assessed quality of the impedance respiration signal. Alternatively, the respiration signal quality may be provided as an input to an alarm arbitration or evaluation algorithm, which may automatically evaluate whether an alarm condition exists or not based at least in part on the signal quality of the impedance respiration signal 52.

Further, the respiration signal quality, when calculated, may be involved in the calculation of the respiration rate for a patient so that the respiration rate estimation incorporates the in-band signal quality indicator logic by construction. For example, once the respiration signal quality is determined, if this indicator is determined to be sufficiently high (such as based upon a specified threshold) for a given window of data (i.e., exceeds a specified quality threshold), the updated PSD template 110 is used to determine a respiration rate 134 for the patient. For example, in one implementation the updated or most recent PSD template is processed (block 130) to identify peaks (such as the three highest peaks) within the PSD template and to determine the respective frequencies associated with each identified peaks.

In addition, the power readings for each identified peak may be determined, where power corresponds to the square of the magnitude of the respective peak. In one implementation, power readings and corresponding frequencies for some or all of the identified peaks (e.g., the top three peaks) are evaluated (block 132) to determine a frequency corresponding to the respiration rate. For example, in one embodiment, the power-weighted average of the frequency components for the three highest power peak readings is determined for the PSD template and corresponds to the respiration frequency (i.e., the respiration rate equals the power-weighted average of the frequency components divided by 60, for a 60 Hz impedance respiration signal 52). In other embodiments, a dominant peak may be determined, such as based on magnitude or power. In such an implementation, the dominant frequency may be divided by 60 to yield the respiration rate as measured in breaths per minute.

Figure 3:
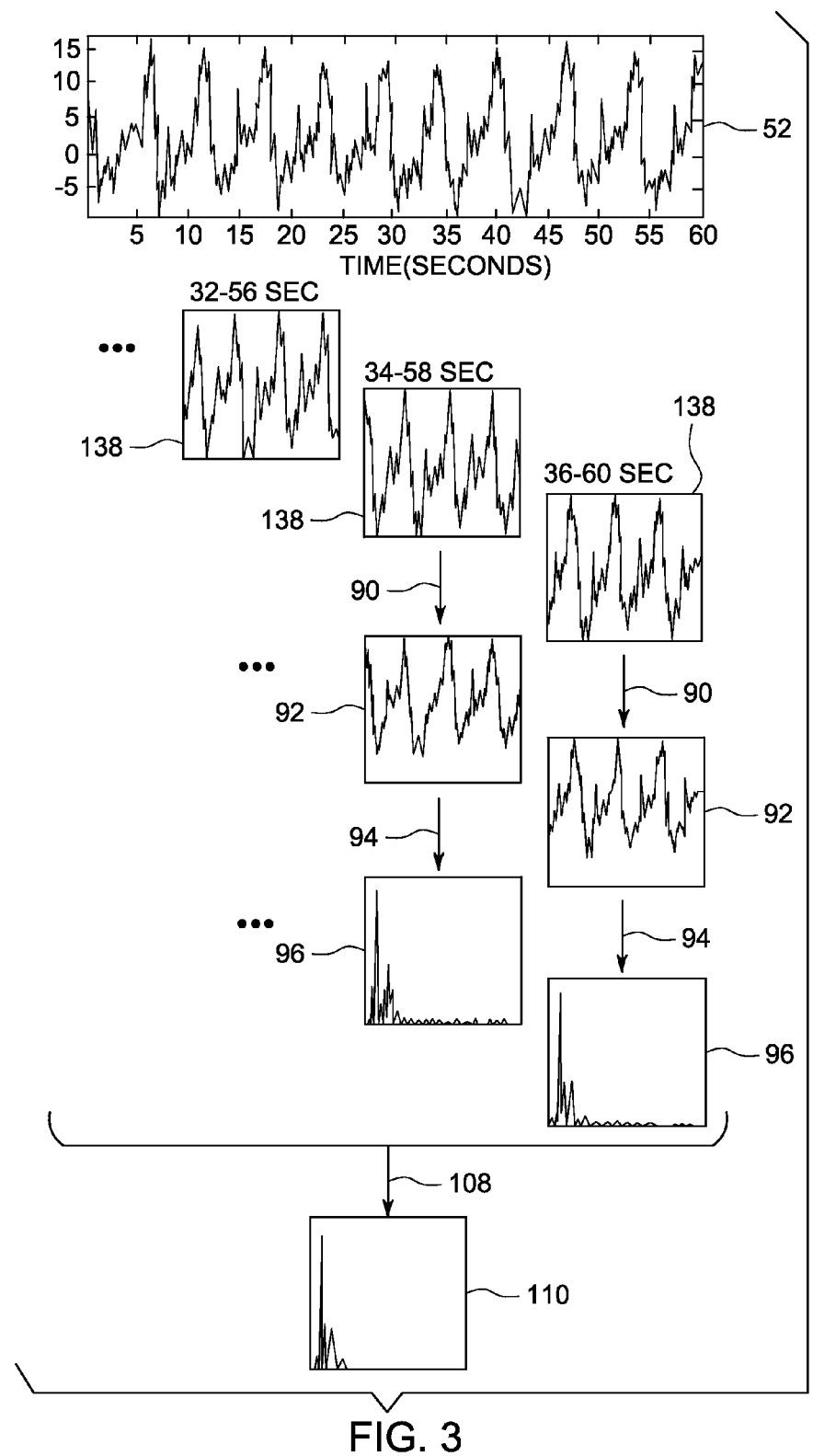
FIG. 3 depicts data transformations associated with steps of the algorithm of FIG. 2, in accordance with aspect of the present disclosure.

The preceding describes examples of algorithms that may be employed in evaluating the signal quality of an impedance respiration signal 52 and/or of calculating a respiration rate 134 using such a signal 52. Turning to FIG. 3, examples of sample data associated with various steps of these algorithms are depicted to further facilitate explanation of these concepts. For example, turning to FIG. 3, an impedance respiration signal 52, represented as a waveform trace, is depicted and represents the raw impedance measurement derived for a patient, such as using a system 10. This impedance respiration signal 52 is, in this example, parsed at 2 second intervals into windows 138 of data having a duration of 24 seconds. That is, every 2 seconds a new window 138 is generated which includes the most recent 24 seconds of impedance respiration data.

In the depicted example, the impedance respiration data 52 is filtered to separately evaluate the different types of noise artifacts associated with different frequency bands. In this example, the windowed impedance respiration data is shown being filtered 90 using an in-band filter to remove cardiac and baseline wander effects, leaving windowed data that has been in-band filtered 92. For each window 92 of filtered impedance respiration data, a power spectral density (PSD) plot 96 is generated 94, such as by performing fast Fourier transform of the respective window of filtered data.

Each PSD plot 96 may be evaluated to determine whether the data in question is noisy or not noisy in view of recent data history. That is, each PSD plot 96 is determined to be noisy or not noisy, as discussed with respect to block 98 of FIG. 2. If a PSD plot 96 is deemed to not be noisy, the PSD plot 96 is used to update 108 a current template of PSD data, thereby generating an updated PSD template 110 that may be used in the determination of a respiration rate 134, such as by identifying a dominant peak or a power-weighted peak average in the PSD template 1100. Conversely, if the current PSD plot is determined to be noisy, the current PSD template is not updated.

Figure 4:
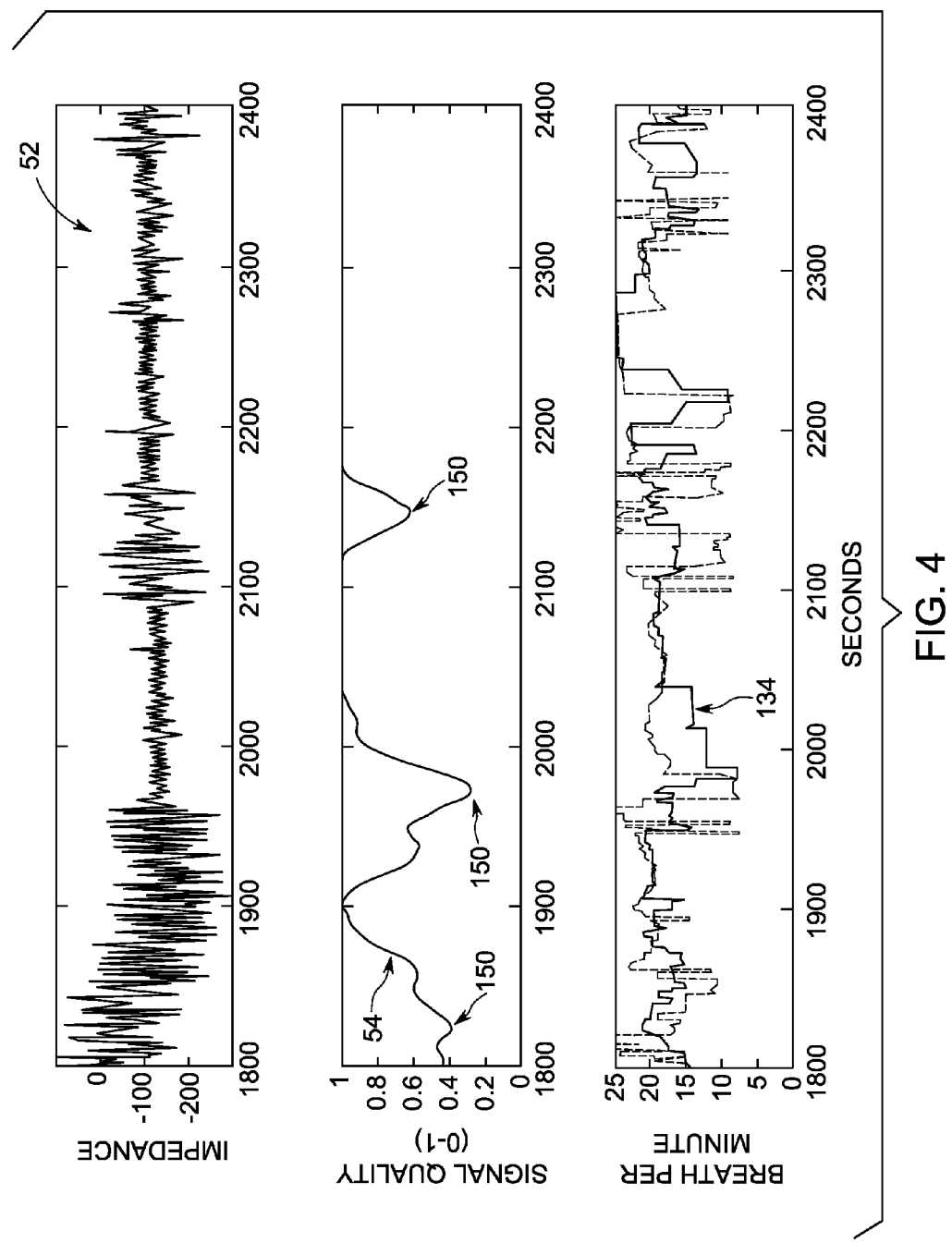
FIG. 4 depicts examples of a signal quality indicator and respiration rate calculated for a first sample of data in accordance with aspect of the present disclosure.
Figure 5:
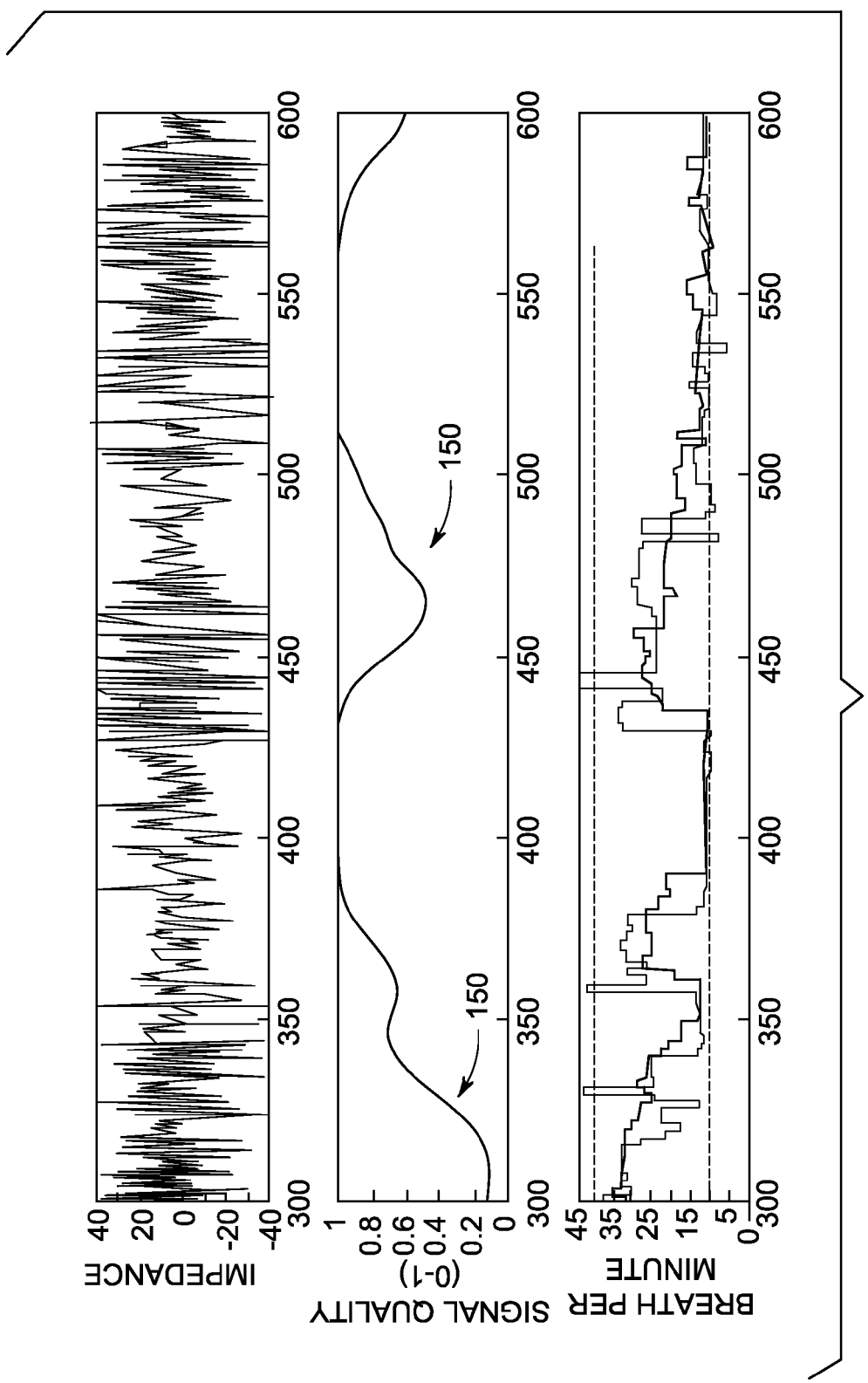
FIG. 5 depicts examples of a signal quality indicator and respiration rate calculated for a second sample of data in accordance with aspect of the present disclosure.
Figure 6:
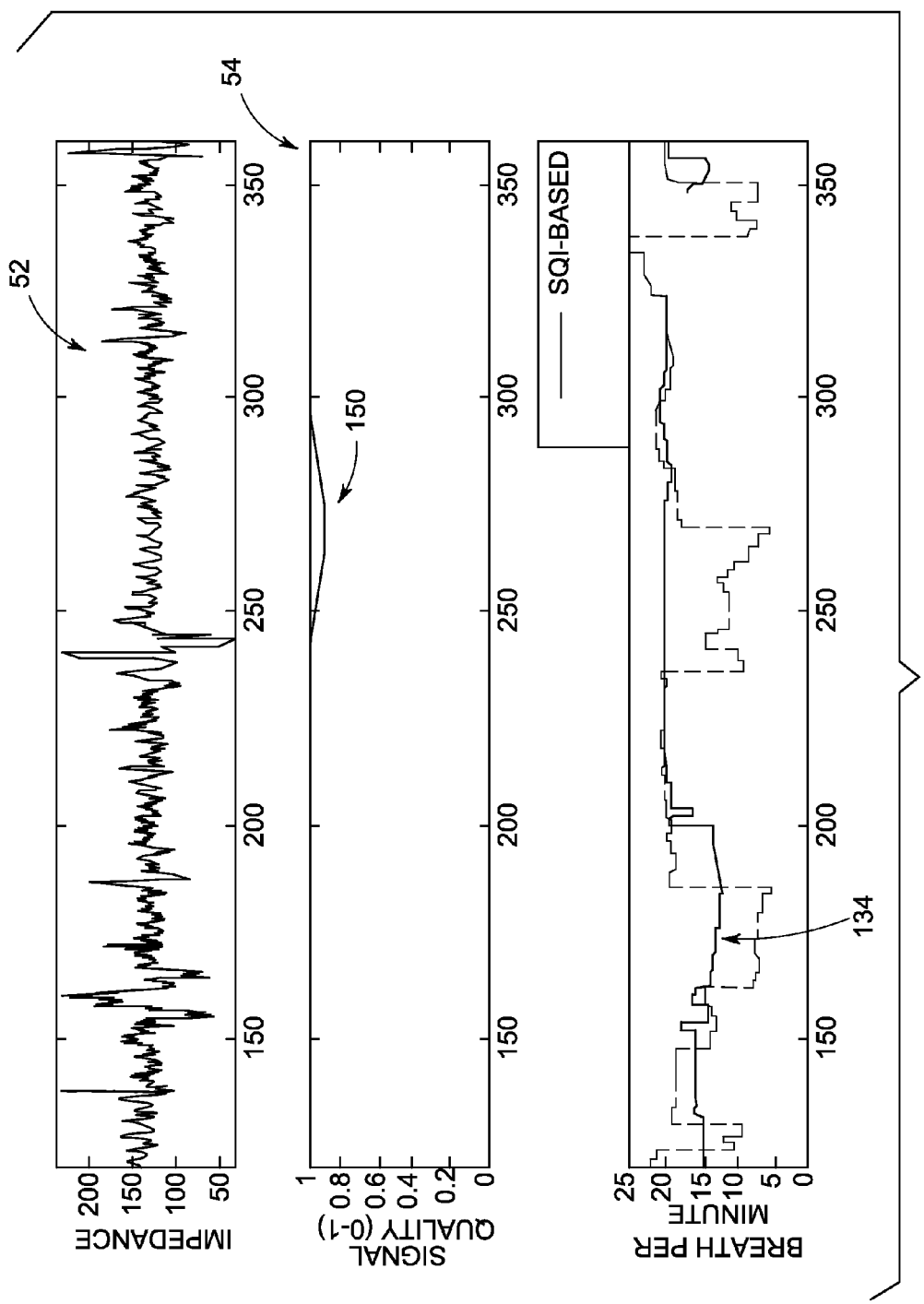
FIG. 6 depicts examples of a signal quality indicator and respiration rate calculated for a third sample of data in accordance with aspect of the present disclosure.

With the foregoing discussion of the operation of the signal quality measures and respiration rate algorithms in mind, the present algorithms were tested on actual patient data. In particular, continuous respiration waveforms data collected at 60 samples per second (i.e., 60 Hz) were acquired. FIGS. 4-6 depict example results of the use of the present approach in processing different sets of the sample data.

In FIGS. 4 and 5, the impedance respiration signal 52 contains high-frequency noise that result in periods 150 of low signal quality. Conversely, in FIG. 6, the impedance respiration signal 52 does not contain substantial high-frequency noise, but does contain brief periods of low-frequency artifacts, which cause a minor drop 150 is signal quality. As can be seen in these examples, the signal quality indicator values 54 are less volatile than the raw impedance respiration signal waveform 52 because of the moving average windows that accumulate effects of brief periods of artifacts over time, thereby smoothing the signal associated with the indicator 54.

Technical effects of the invention include the calculation of a respiration rate from an impedance respiration signal. In certain embodiments, a processing component of a monitor executes routines for calculating the respiration rate, such as routines that filter the impedance respiration signal into at least an in-band signal. The executed routines may calculate a power spectral density for windowed intervals of the in-band signal and, for each window, may make a determination of whether the power spectral density for the respective window is indicative of noisy data or not. A power spectral density template is updated based upon the in-band signal quality measure. The updated power spectral density template may be processed to identify peaks within the template, along with associated frequencies and powers. Based upon the identified peaks within the power spectral density function, a respiration rate is determined.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for deriving a signal quality metric, comprising:
    acquiring an impedance respiration signal;
    generating a series of sets of windowed data from the impedance respiration signal, wherein each window of data comprises data points acquired over a specified duration and is offset from a preceding window by a fixed interval;
    filtering the impedance respiration signal through at least an in-band filter to generate an in-band filtered signal;
    for each window of in-band filtered signals, generating a respective power spectral density;
    determining whether the respective power spectral density for a current window is noisy or not noisy;
    if the respective power spectral density for the current window is not noisy, updating a previous power spectral density template based on the respective power spectral density for the current window to generate a current power spectral density template, wherein the respective power spectral density for the current window is weighted greater than the previous power spectral density template when generating the current power spectral density;
    if the respective power spectral density for the current window is noisy, not updating the previous power spectral density template;
    identifying at least one peak and the corresponding frequencies and powers associated with the identified peaks within the current power spectral density template; and
    determining a respiration rate based on the at least one identified peak.

2. The method of claim 1, wherein the impedance respiration signal is acquired at 60 Hz or an integer multiple of 60 Hz.

3. The method of claim 1, wherein the specified duration is approximately 24 seconds.

4. The method of claim 1, wherein the specified duration comprises an interval in which two breaths are determined to occur within the specified duration.

5. The method of claim 1, wherein the fixed interval comprises 2 seconds.

6. The method of claim 1, wherein filtering the impedance respiration signal comprises filtering the impedance respiration signal though at least one infinite impulse response filter.

7. The method of claim 1, wherein determining whether the respective power spectral density for the current window is noisy or not noisy, comprises:
    determining a correlation vector using a set of stored power spectral density templates; and
    determining whether a statistical descriptor of the correlation vector exceeds a specified threshold;

wherein the respective power spectral density for the current window is determined to be noisy if the statistical descriptor of the correlation vector does not exceed the specified threshold; and wherein the respective power spectral density for the current window is determined to not be noisy if the statistical descriptor of the correlation vector does exceed the specified threshold.

8. The method of claim 7, wherein the statistical descriptor is one of a mean, a median, a mode, a minimum, or a maximum.

9. The method of claim 1, wherein determining the respiration rate comprises:
determining a power-weighted average of the frequency components for a plurality of identified peaks; and
determining a respiration rate from the power weighted average.

10. The method of claim 1, wherein determining the respiration rate comprises:
determining a dominant peak within the current power spectral density template; and
determining a respiration rate based on the dominant peak.

11. A non-transitory, computer-readable medium configured to store one or more routines executable by a processing system, the routines, when executed, causing acts to be performed comprising:
applying an in-band filter to an impedance respiration signal to generate an in-band filtered signal;
generating a respective power spectral density for each of a series of windows of the in-band filtered signal, wherein each window comprises data points acquired over a specified duration and is offset from adjacent windows by a fixed interval;
processing the respective power spectral density for each window in sequence to determine whether the respective power spectral density for each window is noisy or not noisy;
updating, if the respective power spectral density for a current window is not noisy, a previous power spectral density template based on the respective power spectral density for the current window to generate a current power spectral density template; and
determining a respiration rate based on one or more peaks identified in the current power spectral density template, wherein determining the respiration rate comprises:
determining a power-weighted average of frequency components for a plurality of identified peaks; and
determining a respiration rate from the power weighted average.

12. The non-transitory, computer-readable medium of claim 11, wherein determining whether the respective power spectral density for each window is noisy or not noisy, comprises:
determining a correlation vector using a set of stored power spectral density templates; and
determining whether a statistical descriptor of the correlation vector exceeds a specified threshold;
wherein the power spectral density for the respective window is determined to be noisy if the statistical descriptor of the correlation vector does not exceed the specified threshold; and
wherein the power spectral density for the respective window is determined to not be noisy if the statistical descriptor of the correlation vector does exceed the specified threshold.

13. The non-transitory, computer-readable medium of claim 11, wherein determining the respiration rate comprises:
determining a dominant peak within the current power spectral density template; and
determining a respiration rate based on the dominant peak.

14. A physiological monitoring system, comprising:
a memory storing one or more routines; and
a processing component configured to execute the one or more routines stored in the memory, wherein the one or more routines, when executed by the processing component, cause acts to be performed comprising:
acquiring an impedance respiration signal;
generating a series of data windows from the impedance respiration signal, wherein each data window comprises data points acquired over a specified duration and is offset from a preceding window by a fixed interval;
filtering the impedance respiration signal through at least an in-band filter to generate an in-band filtered signals;
generating a respective power spectral density for each window of in-band filtered signals;
determining whether the respective power spectral density for a current window is noisy or not noisy;
updating, if the respective power spectral density for the current window is not noisy, a previous power spectral density template based on the respective power spectral density for the current window to generate a current power spectral density template wherein the respective power spectral density for the current window is weighted greater than the previous power spectral density template when generating the current power spectral density; and
determining a respiration rate based the current power spectral density template.

15. The physiological monitoring system of claim 14, wherein determining whether the respective power spectral density for each window is noisy or not noisy, comprises:
determining a correlation vector using a set of stored power spectral density templates; and
determining whether a statistical descriptor of the correlation vector exceeds a specified threshold;
wherein the respective power spectral density for the current window is determined to be noisy if the statistical descriptor of the correlation vector does not exceed the specified threshold; and
wherein the respective power spectral density for the current window is determined to not be noisy if the statistical descriptor of the correlation vector does exceed the specified threshold.

16. The physiological monitoring system of claim 14, wherein determining the respiration rate comprises:
determining a power-weighted average of frequency components for a plurality of identified peaks within the current power spectral density template; and
determining a respiration rate from the power weighted average.

17. The physiological monitoring system of claim 14, wherein determining the respiration rate comprises:
determining a dominant peak within the current power spectral density template; and
determining a respiration rate based on the dominant peak.

18. The physiological monitoring system of claim 14, wherein the physiological monitoring system comprises one of an impedance respiration monitor or an electrocardiography (ECG) monitor.

\* \* \* \* \*